United States Patent
Wine et al.

(10) Patent No.: US 11,684,755 B2
(45) Date of Patent: Jun. 27, 2023

(54) MEDICAL CONNECTORS HAVING INTEGRATED ADHESIVE BACKING

(71) Applicant: CareFusion 303, Inc., San Diego, CA (US)

(72) Inventors: Jason Andrew Wine, Placentia, CA (US); Chris Jesse Zollinger, Chino Hills, CA (US)

(73) Assignee: CareFusion 303, Inc., San Diego, CA (US)

( * ) Notice: Subject to any disclaimer, the term of this patent is extended or adjusted under 35 U.S.C. 154(b) by 153 days.

(21) Appl. No.: 17/030,058

(22) Filed: Sep. 23, 2020

(65) Prior Publication Data
US 2022/0088351 A1    Mar. 24, 2022

(51) Int. Cl.
*A61M 25/02* (2006.01)
*A61M 25/06* (2006.01)

(52) U.S. Cl.
CPC ........ *A61M 25/02* (2013.01); *A61M 25/0606* (2013.01); *A61M 2025/0253* (2013.01); *A61M 2205/02* (2013.01)

(58) Field of Classification Search
CPC .............. A61M 25/02; A61M 25/0606; A61M 2025/0253; A61M 2205/02; A61M 2025/0266; A61M 5/1418; A61M 2025/026; A61M 2025/0206; A61M 2025/0213; A61F 13/0269; A61F 13/0246; A61F 13/025; A61F 13/0253; A61F 13/02
See application file for complete search history.

(56) References Cited

U.S. PATENT DOCUMENTS

| | | | |
|---|---|---|---|
| 5,236,421 A | 8/1993 | Becher | |
| 6,231,547 B1* | 5/2001 | O'Hara | A61M 25/02 604/174 |
| 2009/0157000 A1 | 6/2009 | Walker | |
| 2013/0123678 A1* | 5/2013 | Carty | A61F 13/0253 602/54 |
| 2020/0230366 A1 | 7/2020 | Spataro et al. | |

(Continued)

FOREIGN PATENT DOCUMENTS

WO    WO-2021154283 A1    8/2021

OTHER PUBLICATIONS

Parris, Lisa, What Gets Medical Tape Adhesive Off Skin?, Jul. 27, 2017, Healthfully, p. 1 (Year: 2017).*

(Continued)

*Primary Examiner* — Katherine H Schwiker
*Assistant Examiner* — Phoebe Anne Staton
(74) *Attorney, Agent, or Firm* — Morgan, Lewis & Bockius LLP

(57) ABSTRACT

A holder for securing a venous access device to a patient may include a flexible substrate having an upper surface, a lower surface, and an outer perimetal surface. An adhesive layer may overlay the lower surface of the flexible substrate. The adhesive layer may have an adhesive for adhering to skin of the patient. The holder may further include a hydrophilic matrix integrated into at least a portion of the adhesive layer, at least one solvent reservoir disposed on the upper surface of the flexible substrate, and a connector secured to the outer perimetal surface. The connector may have a first end for connection to a needle assembly and a second end for connection to an IV fluid line.

6 Claims, 5 Drawing Sheets

(56) References Cited

U.S. PATENT DOCUMENTS

2021/0236777 A1* 8/2021 Chelak .................. A61M 39/12
2022/0273914 A1* 9/2022 Roche Rebollo ............................
                                                A61M 25/09041

OTHER PUBLICATIONS

International Search Report and Written Opinion for Application No. PCT/US2021/051144, dated Jan. 25, 2022, 13 pages.

* cited by examiner

MEDICAL CONNECTORS HAVING INTEGRATED ADHESIVE BACKING

TECHNICAL FIELD

The present disclosure relates generally to securement devices for stabilizing venous access devices, and, in particular, to a holder having an integrated adhesive backing for securing venous access devices such as intravenous needles and their associated luer fittings to a patient's skin.

BACKGROUND

Intravenous (IV) needles are frequently used in medical procedures. As with any invasive procedure, IV-related infections are a significant concern. Where repeated access to the bloodstream is needed, IV catheters are used. These catheters frequently use cylindrical Luer fittings and valves as an alternative to traditional needle based injection ports. However, in order to be effective, catheters must avoid dislodgment as well as avoid bloodstream infection and local site infection.

IV catheter securement poses a number of challenges. In order to maximize residence time, IV catheters must be secured from dislodgement or causing damage from unwanted movement. The insertion site should also be easily inspected for and protected from contamination or infection. Preferably, the catheter port can also be readily serviced.

Traditional methods call for securing the catheter insertion site with a gauze dressing or a transparent film with adhesive tape. Adhesive tape is problematic in that it is difficult to keep sterile and is prone to irritate a patient's skin. The use of a transparent film is preferable since it serves as a pathogenic barrier and permits viewing of the insertion site. However, transparent films are problematic in that the film eventually loosens from casual contact and permits catheter migration.

The disparity in diameter between an IV needle and a Luer fitting further complicates the securement problem. While an adhesive strip can be taped over the Luer fitting to secure the luer fitting to the skin, the opaque tape prevents visual inspection of the Luer fitting. Moreover, securing the Luer fitting under a transparent film or under adhesive tape is problematic in that the larger diameter of the Luer fitting acts as a spacer and creates a gap between the film or tape and the patient's skin. This gap compromises the infection barrier purpose of securement.

The description provided in the background section should not be assumed to be prior art merely because it is mentioned in or associated with the background section. The background section may include information that describes one or more aspects of the subject technology.

SUMMARY

According to various embodiments of the present disclosure, a holder for securing a venous access device to a patient may include a flexible substrate having an upper surface, a lower surface, and an outer perimetal surface. An adhesive layer may overlay the lower surface of the flexible substrate. The adhesive layer may have an adhesive for adhering to skin of the patient. The holder may further include a hydrophilic matrix integrated into at least a portion of the adhesive layer, at least one solvent reservoir disposed on the upper surface of the flexible substrate, and a connector secured to the outer perimetal surface. The connector may have a first end for connection to a needle assembly and a second end for connection to an IV fluid line.

According to various embodiments of the present disclosure, a method of assembling a holder for securing a venous access device to a patient may include selecting a flexible substrate including a breathable material, and placing an adhesive layer over a lower surface of the flexible substrate. The adhesive layer may have an adhesive for adhering to skin of the patient. The method may further include fluidly coupling at least one solvent source to the adhesive layer, and securing a connector to an outer perimetal surface of the flexible substrate. The connector may have a first end for connection to a needle assembly and a second end for connection to an IV fluid line.

According to various embodiments of the present disclosure, a holder for securing a venous access device to a patient may include a flexible substrate having an upper surface and a lower surface, a solvent delivery line coupled to the upper surface of the flexible substrate, and an adhesive layer overlaying the lower surface of the flexible substrate. The adhesive layer may include an adhesive for adhering to skin of the patient. The holder may further include a solvent pathway integrated into at least a portion of the adhesive layer, and a connector secured to the upper surface. The solvent pathway may include at least one aperture for fluidly connecting the solvent delivery line and the solvent pathway. The connector may include a first end for connection to a needle assembly and a second end for connection to an IV fluid line.

It is to be understood that both the foregoing general description and the following detailed description are exemplary and explanatory and are intended to provide further explanation of the subject technology as claimed. It is also to be understood that other aspects may be utilized, and changes may be made without departing from the scope of the subject technology.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
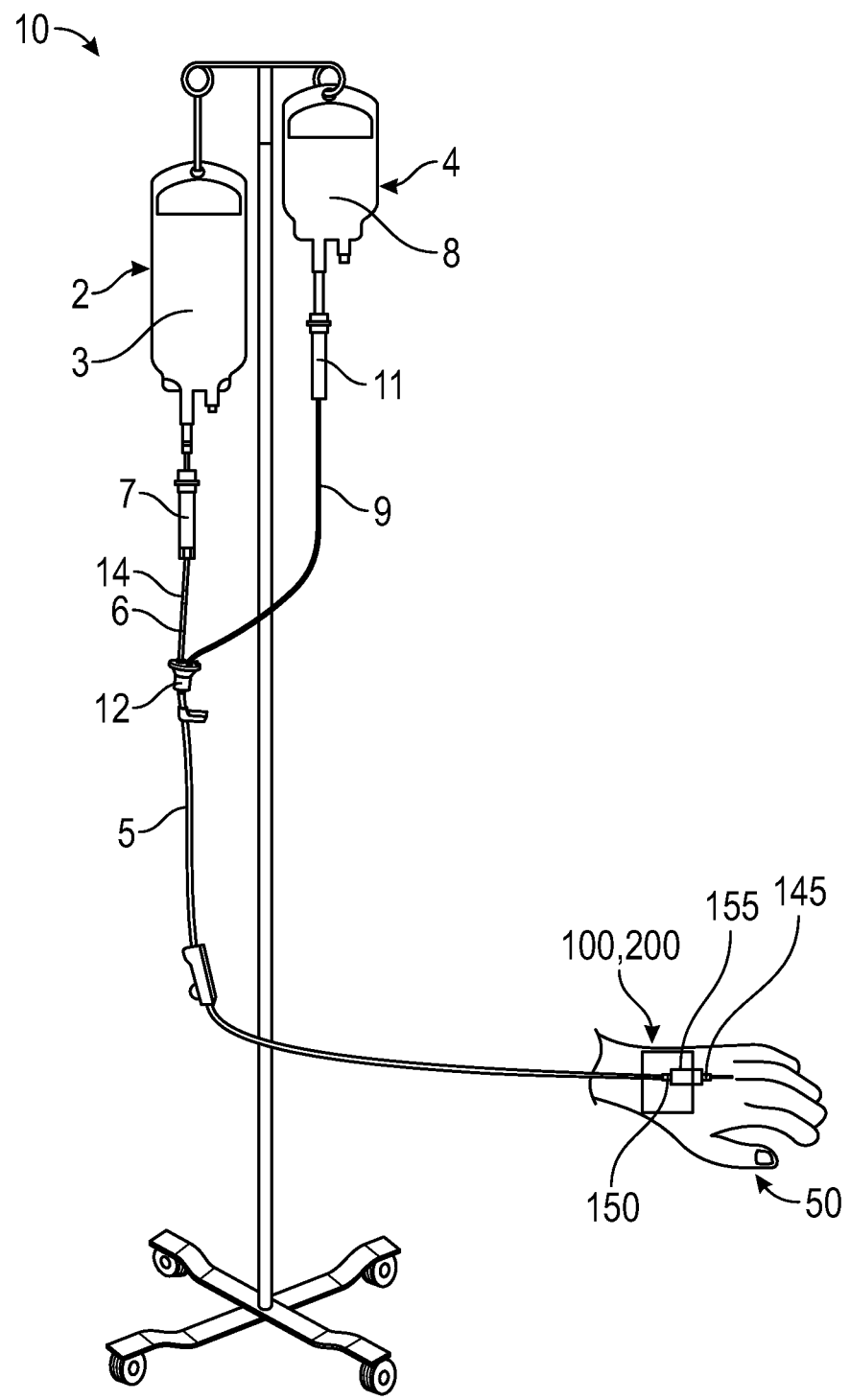
FIG. 1 is a perspective view of an IV set including a holder for securing a venous access device, in accordance with some embodiments of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Various embodiments of the present disclosure are generally directed to securement devices for stabilizing venous access devices, and, in particular, to a holder having an integrated adhesive backing for securing venous access devices such as intravenous needles and their associated luer fittings to a patient's skin.

As used herein, the terms "medical connector," "connector," "fitting," and any variation thereof refer to any device used to provide a fluid flow path between fluid lines coupled thereto. For example, the medical connector may be or include a bond pocket or other types of connectors. Additionally, the terms "medical connector," "connector," "fitting," and any variation thereof refer to any device used to deliver liquids, solvents, or fluids to or from a patient under medical care. For example, the medical connector may be used for intravenous (IV) delivery of fluids, fluid drainage, oxygen delivery, a combination thereof, and the like to the patient.

In some embodiments, a holder may include a flexible substrate having an upper surface, a lower surface, and an outer perimetal surface. A connector (e.g., a male luer lock fitting) may be coupled to a surface of the flexible substrate for connecting to a venous access device in order to secure the venous access device to the patient via the holder. An adhesive layer or backing may overlay the lower surface of the flexible substrate. The adhesive layer or backing 120 may be coated, adhered, fastened or otherwise attached to the lower surface of the flexible substrate. The adhesive layer or backing may include an adhesive for adhering the holder having an intravenous needle assembly and associated connector (e.g., luer lock fitting) to skin of the patient. A hydrophilic matrix may integrated into the adhesive backing. One or more solvent reservoirs containing a solvent deleterious to the adhesive but safe for skin contact may be disposed on the upper surface of the flexible substrate. The one or more solvent reservoirs may each have a hollow interior which is fluidly communicated with the hydrophilic matrix that is integrated into the adhesive layer or backing. A barrier may be included between the hydrophilic matrix and each solvent reservoir. Prior to removal from the patient's skin, the barrier may be removed and the solvent allowed to absorb throughout the hydrophilic matrix. The solvent may then begin to dissolve the adhesive bonding the connector and to the patient's skin. After the solvent has been allowed to break down the adhesive, the clinician may be able to remove the luer lock fitting from the patient's skin without causing damage or pain.

In some embodiments, a holder may include a flexible substrate, an adhesive layer or backing overlaying a lower surface of the flexible substrate, a solvent pathway may be integrated into at least a portion of the adhesive layer or backing. The holder may further include at least one solvent delivery line coupled to an upper surface of the flexible substrate. The solvent delivery line may be configured to transport a solvent from a solvent source (e.g., a syringe) into the solvent pathway. Accordingly, the solvent pathway may be provided for the clinician to inject the dissolving solvent onto the surface of the skin and thereby weaken the adhesive bond. As the clinician injects the fluid, the flexible substrate will balloon, allowing the fluid to reach further parts of the adhesive and gently dissolve & peel away the adhesive layer throughout the holder.

The aforementioned holder configurations are advantageous over prior art dressings and adhesive methods (e.g., taping) of needles and needle assemblies which directly adhere the needle assembly and associated connector (e.g., male luer lock fitting) to the patient's skin. For example, by incorporating the securement mechanism in the male luer lock fitting (i.e., by connecting the needle assembly to the holder 100 via the luer lock fitting and then attaching the holder to the patient), further isolation may be provided in cases where the needle assembly that is being used contains a short extension tube. Given the aforementioned configuration of the holder, the short extension tube may filter out small dynamic loads and thereby not impart these loads onto the needle assembly that is inserted into the patient.

FIG. 1 is a perspective view of an IV set including a medical connector in accordance with some embodiments of the present disclosure. As illustrated in FIG. 1, an IV set 10 includes the holder 100, 200 therein. IV set 10 includes a main fluid system 2 and an auxiliary fluid system 4. An IV pump (not shown) receives fluid from main fluid system 2 and branch or auxiliary fluid system 4 via a supply line 5 and controls and dispenses the fluids therefrom to a patient 50.

Main fluid system 2 includes a main fluid source such as a fluid bag 3 which may include or contain saline solution or other fluid to be administered to the patient. As illustrated, tube 6 carries flow from a drip chamber 7 to a Y-connector 12. Check valve 14 is disposed in tube 6 upstream from the Y-connector 12 and enables flow from fluid bag 3 to the IV pump (not illustrated) while preventing reverse flow (backflow) of fluid from auxiliary fluid system 4 toward fluid bag 3.

Auxiliary fluid system 4 includes an auxiliary fluid source such as a fluid bag 8, which may contain drugs or other fluid to be supplied to the patient for treatment. An auxiliary fluid line 9 carries flow from drip chamber 11 to the Y-connector 12.

The present disclosure relates generally to securement devices for stabilizing venous access devices, and, in particular, to a holder having an integrated adhesive backing for securing venous access devices such as intravenous needles and their associated luer fittings to a patient's skin.

Figure 2:
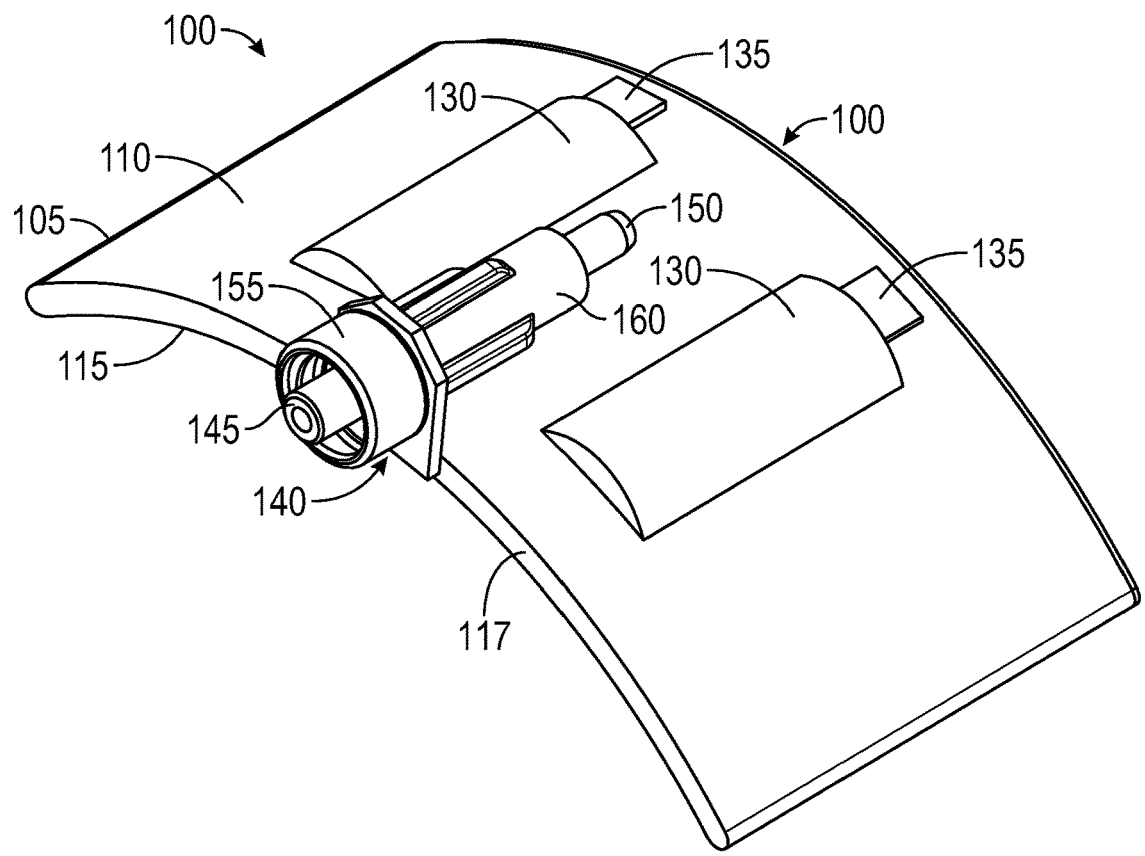
FIG. 2 is a perspective view of a holder for securing a venous access device, in accordance with some embodiments of the present disclosure.
Figure 3:
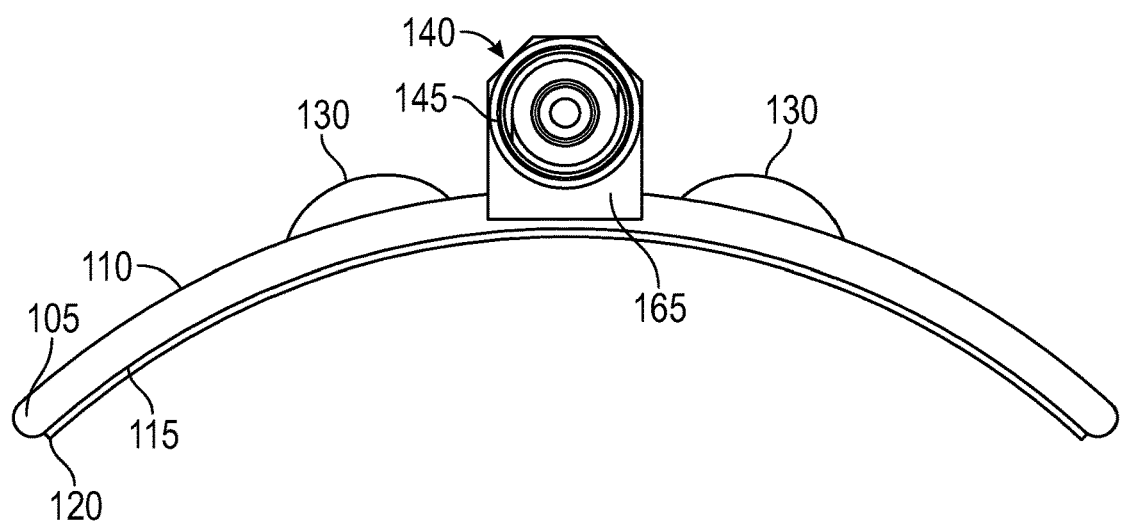
FIG. 3 is a front view of the holder of FIG. 2, in accordance with some embodiments of the present disclosure.

FIG. 2 is a perspective view of a holder 100 for securing a venous access device, in accordance with some embodiments of the present disclosure. FIG. 3 is a front view of the holder of FIG. 2, in accordance with some embodiments of the present disclosure. Referring to FIG. 2, the holder 100 may include a flexible substrate 105 having an upper surface 110, a lower surface 115, and an outer perimetal surface 117. In some embodiments, the flexible substrate 105 may be formed of a urethane or similar material which is flexible, clear, breathable and sterilizable to minimize contamination when the IV holder 100 is applied to the patient's skin. In some embodiments, the flexible substrate 105 may be formed of or include at least one of foam, silicone, soft plastic, rubber or elastomers.

As illustrated in FIG. 3, an adhesive layer or backing 120 may overlay the lower surface 115 of the flexible substrate 105. In some embodiments, the adhesive layer or backing 120 may be adhered, fastened or otherwise attached to the lower surface 115 of the flexible substrate 105. However, the various embodiments of the present disclosure are not limited to the aforementioned configuration. In some embodiments, the adhesive layer or backing 120 may be in the form of a coating, for example, an adhesive coated onto the lower surface 115 of the flexible substrate 105. The adhesive layer or backing 120 may include an adhesive for adhering the holder 100 having an intravenous needle assembly and associated connector (e.g., Luer fitting) to skin of the patient 50.

Figure 4:
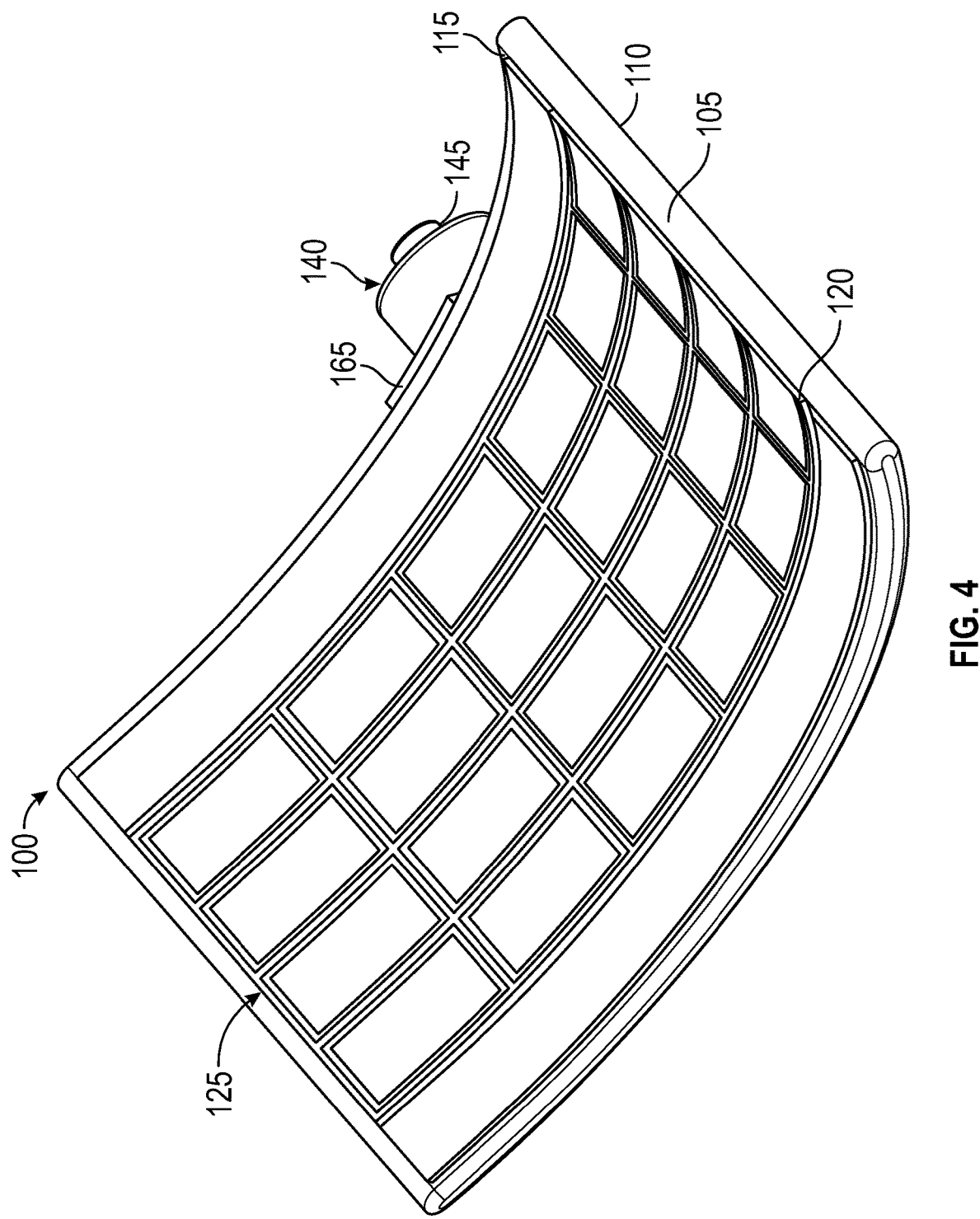
FIG. 4 is a bottom view of the holder of FIG. 2, in accordance with some embodiments of the present disclosure.

FIG. 4 is a bottom view of the holder of FIG. 2, in accordance with some embodiments of the present disclosure. In some embodiments, a hydrophilic matrix 125 may be integrated into at least a portion of the adhesive layer or backing 120. As depicted, the hydrophilic matrix 125 is integrated throughout the adhesive layer or backing 120. However, the various embodiments of the present disclosure are not limited to the aforementioned configuration. In some embodiments, the hydrophilic matrix 125 may be integrated into only a portion of the adhesive layer or backing 120.

Figure 5:
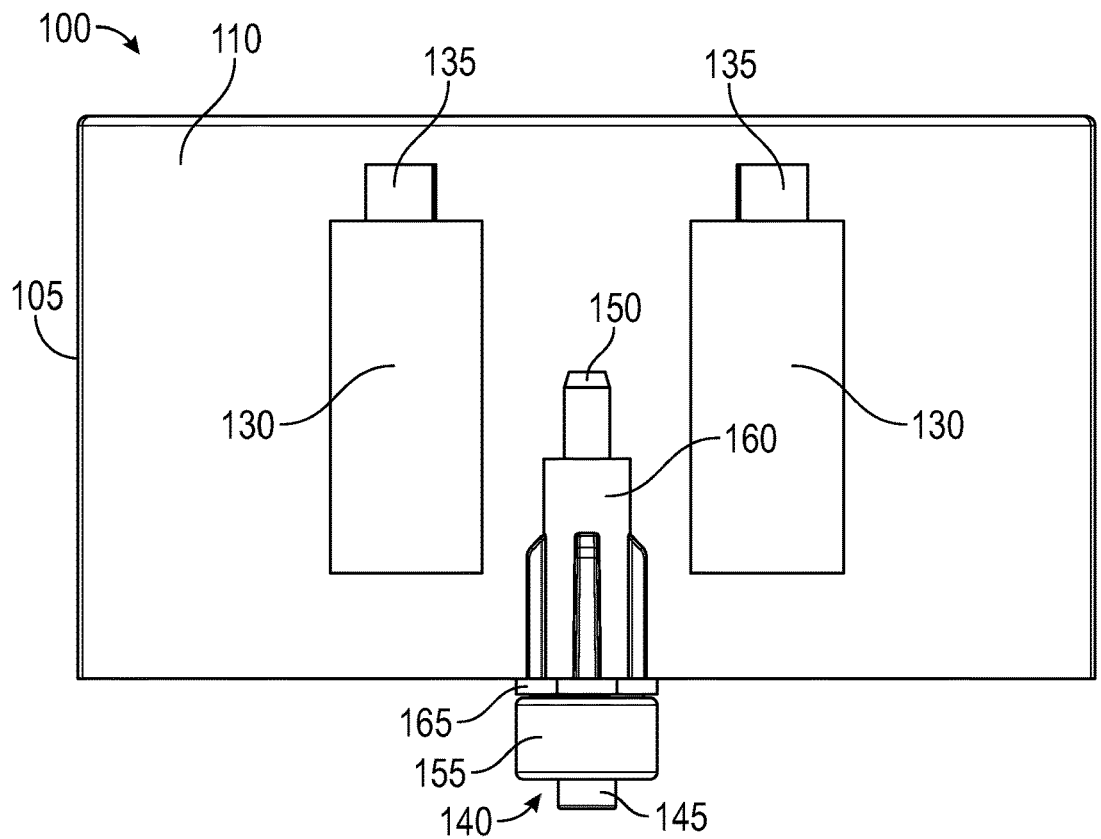
FIG. 5 is a top view of the holder of FIG. 2, in accordance with some embodiments of the present disclosure.
Figure 6:
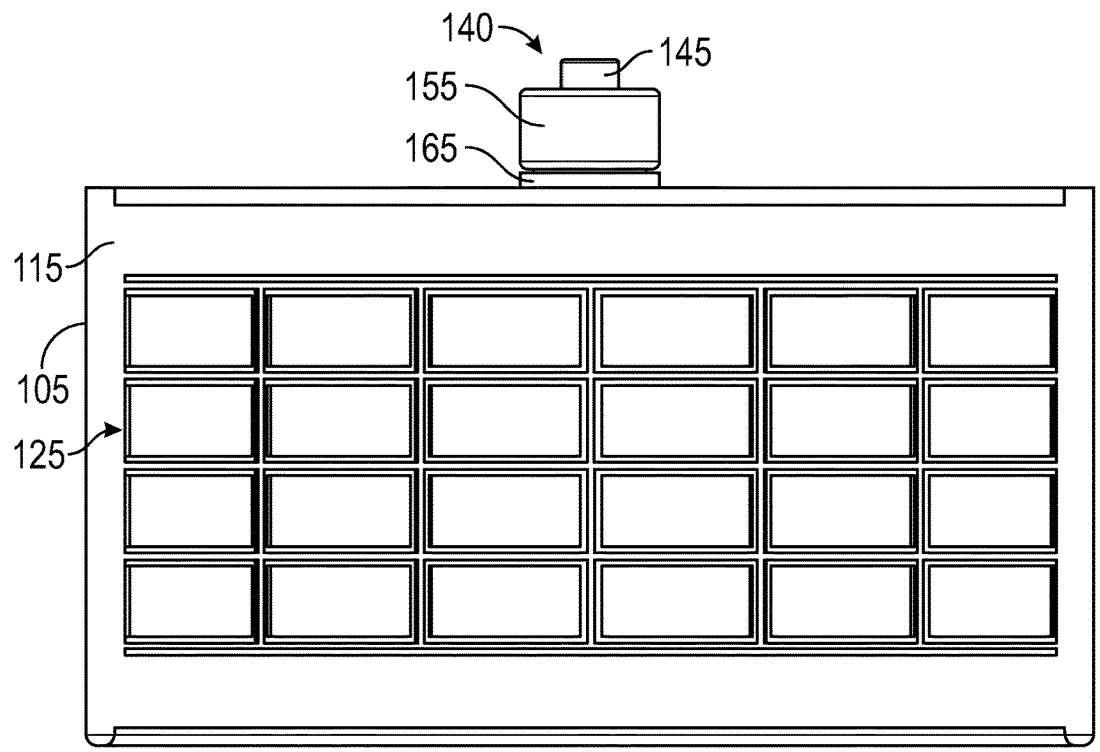
FIG. 6 is a bottom view of the holder connector of FIG. 2, in accordance with some embodiments of the present disclosure.

FIG. 5 is a top view of the holder of FIG. 2, in accordance with some embodiments of the present disclosure. FIG. 6 is a bottom view of the holder connector of FIG. 2, in accordance with some embodiments of the present disclosure. In some embodiments, the holder 100 may include at least one solvent reservoir 130 disposed on the upper surface 110 of the flexible substrate 105. As depicted, two solvent reservoirs 130 may be disposed on the upper surface 110. The various embodiments of the present disclosure however are not limited to the aforementioned configuration. In some embodiments, the holder may include only one solvent reservoir. In yet other embodiments, the holder 100 may include more than two solvent reservoirs 130. The solvent reservoirs may be a cylindrical body configured with a hollow interior for containing a solvent therein. Although the solvent reservoirs 130 are depicted as being cylindrical in shape, the various embodiments of the present disclosure are not limited to this configuration. In other embodiments, the solvent reservoirs 130 may be of any shape such as circular, rectangular or other polygonal shapes. The solvent reservoirs 130 may contain a solvent capable of breaking down or otherwise dissolving the adhesive in the adhesive layer or backing 105 when the solvent is absorbed into the hydrophilic matrix, as shall be described in further detail below. In some embodiments, the solvent may be isopropyl alcohol.

In some embodiments, the at least one solvent reservoir 130 may have a hollow interior which is fluidly communicated with the hydrophilic matrix 125 that is integrated into the adhesive layer or backing 120. For example, the flexible substrate 105 may include a cut-out or longitudinally extending aperture at a position corresponding to the position of each solvent reservoir 130. Accordingly, solvent contained in the solvent reservoirs 130 may flow and be absorbed into the hydrophilic matrix 125 of the adhesive layer or backing 120. Prior to removal of the holder 100 from a patient's skin, a barrier 135 having a shape and size corresponding to the aperture which fluidly communicates the solvent reservoirs 130 and the adhesive layer or backing 120, may be interposed between the solvent reservoirs 130 and the adhesive layer or backing 120 in order to close or otherwise block the aperture. Accordingly, fluid communication between the solvent reservoirs 130 and the adhesive layer or backing 120 may be blocked until a time that it is desired to remove the holder 100 from the patient's skin. The barrier 135 may thus act or serve as a removable base of the solvent reservoirs 130, which is removable in order to expose the solvent to the adhesive layer or backing 120.

According to various aspects of the present disclosure, the holder 100 may further include a connector 140 secured to the outer perimetal surface 117 of the flexible substrate. The connector 140 may have a first end 145 for connection to a needle assembly (e.g., a catheter) and a second end 150 for connection to an IV fluid line (e.g. IV supply line 5). For example, the connector 140 may be a luer lock fitting, and in particular may be, but not limited to, a male luer lock fitting. In these embodiments, the first end 145 of the male luer lock fitting may have a spin lock collar 155 for threaded engagement and connection of a needle assembly (e.g., catheter or other needle device) to be inserted into the body of the patient through the skin. Accordingly, a needle assembly may be attached or adhered to the patient's skin via the holder 100. The aforementioned configuration is advantageous over prior art dressings and adhesive methods (e.g., taping) of needles and needle assemblies which directly adhere the needle assembly and associated connector (e.g., male luer lock fitting) to the patient's skin. For example, by incorporating the securement mechanism in the male luer lock fitting (i.e., by connecting the needle assembly to the holder 100 via the luer lock fitting 140 and then attaching the holder 100 to the patient), further isolation may be provided in cases where the needle assembly that is being used contains a short extension tube. Given the aforementioned configuration of the holder 100, the short extension tube may filter out small dynamic loads and thereby not impart these loads onto the needle assembly that is inserted into the patient.

While not strictly necessary, there may be a benefit to be obtained if the holder 100 is longer (i.e., in the Y direction) than it is wide (i.e., in the X direction). A narrower width may provide for better support and securement of the holder 100. Additionally, a longer length may allow for added versatility in the positioning of the holder 100 relative to the luer lock fitting 140.

In operation, a needle assembly (e.g., a catheter or other needle device to be inserted into the body of a patient) may be threadedly engaged to the first end 145 of the luer lock fitting 140 via the spin lock collar 155. The lower surface 115 of holder 100 may then be pressed against the skin of the patient to expose and adhere the adhesive layer or backing 120 to the patient's skin. Accordingly, the needle assembly may be securely attached or adhered to the patient's skin via the holder 100. The IV supply line 5 may then be connected to the second end 150 of the luer lock fitting 140 in order to deliver a fluid or other drug from the IV supply line 5 to the patient via the needle assembly. Once the fluid has been administered to and/or removed from the patient's body via the needle assembly, the holder 100 may be detached from the patient's skin as detailed below.

In the event that it is necessary to detach the needle assembly from the luer lock fitting 140 for service and/or to clear a needle of the needle assembly, the luer lock fitting 140 may be unthreaded from the needle assembly via the spin lock collar 155.

When it is desired to remove the holder 100 from the patient's skin, the barrier 135 may be removed thereby opening fluid connection between the solvent chambers 130 and the adhesive layer or backing 120. Accordingly, the solvent may flow from the solvent chambers 130 into the adhesive layer or backing 120. In particular, the solvent may flow into and be absorbed throughout the hydrophilic matrix 125 in the adhesive layer or backing 120. The solvent may then begin to dissolve the adhesive of the adhesive layer or backing 120 which bonds the luer lock fitting 140 to the patient's skin. Since the solvent dissolves and breaks down the adhesive, the clinician or other user may advantageously be able to remove the male luer lock fitting from the patient's skin without causing damage or pain. Further advantageously, by incorporating means for removal of the adhesives as described above, a wider selection of adhesives may be available for use potentially leading to a securement architecture which is improved over current securement devices. For example, the aforementioned method of detaching the holder from the patient's skin may allow a stronger adhesive to be used without risk or hurting or damaging the patient's skin as may be the case with conventional securement methods. Furthermore, the adhesive layer or backing 120 provides a securement method, which further reduces the risk of needle assembly (e.g., catheter or other needle device) dislodgment.

Figure 7:
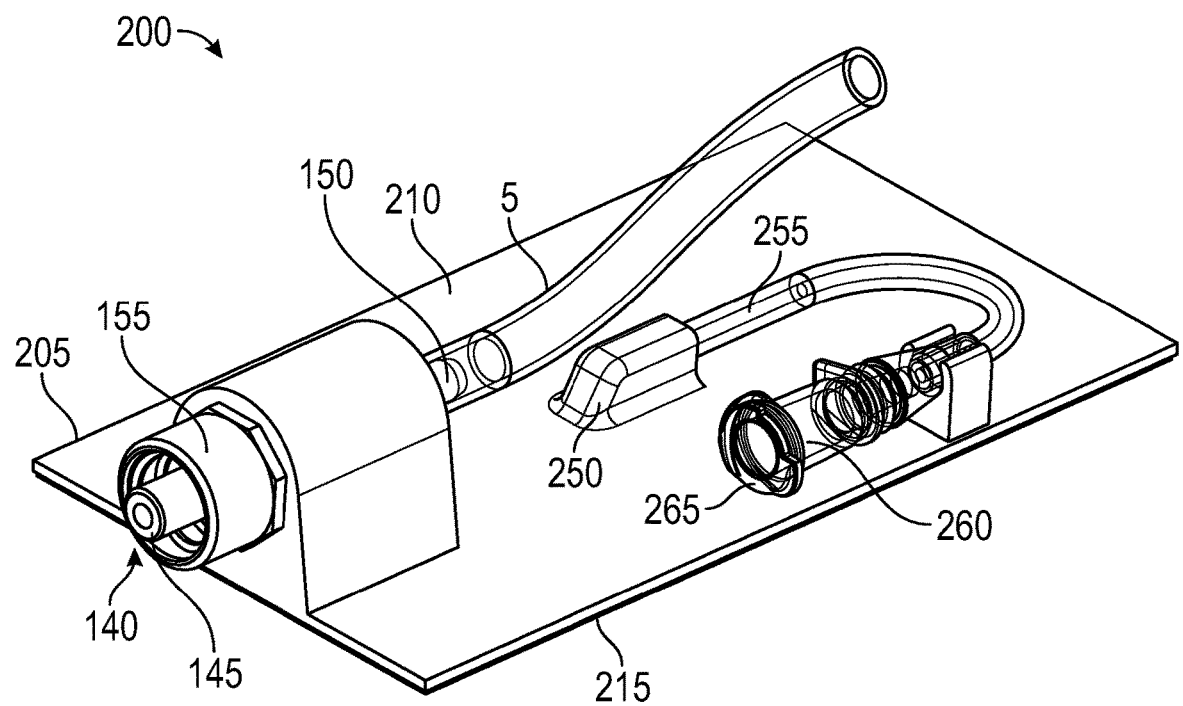
FIG. 7 is a perspective top view of a holder for securing a venous access device, in accordance with some embodiments of the present disclosure.
Figure 8:
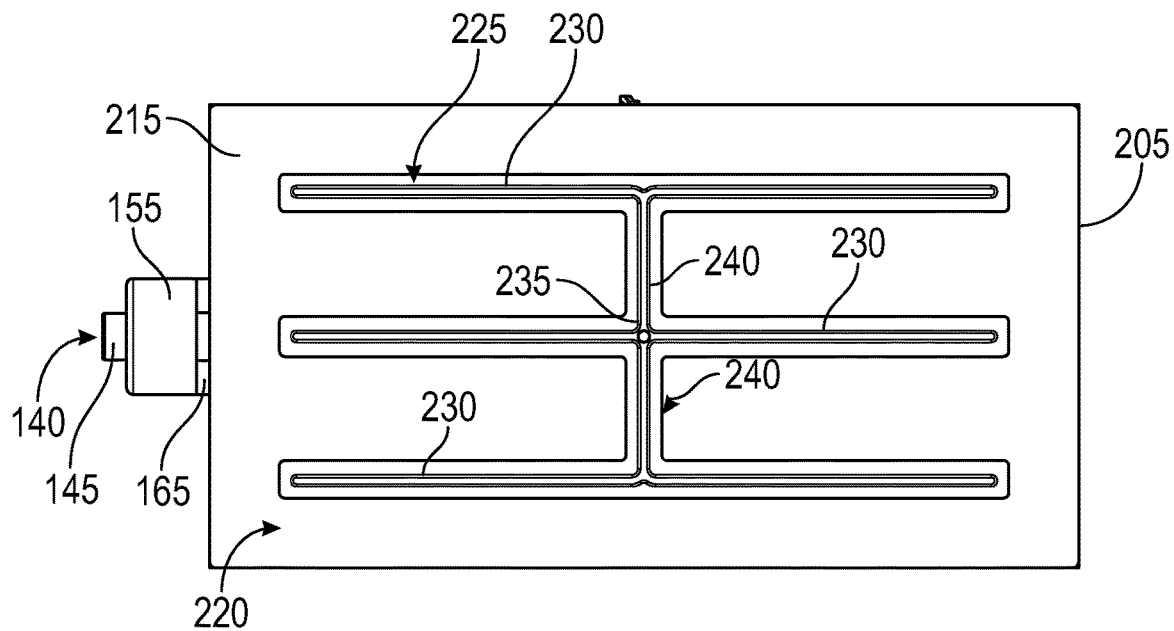
FIG. 8 is a bottom view of the holder of FIG. 7, in accordance with some embodiments of the present disclosure.

FIG. 7 is a perspective top view of a holder 200 for securing a venous access device, in accordance with some embodiments of the present disclosure. FIG. 8 is a bottom view of the holder 200 of FIG. 7, in accordance with some embodiments of the present disclosure. Referring to FIGS. 7 and 8, the holder 200 may include a flexible substrate 205 having an upper surface 210, and a lower surface 215. In some embodiments, the flexible substrate 205 may be formed of a urethane or similar material, which is flexible, clear, breathable and sterilizable to minimize contamination when the IV holder 200 is applied to the patient's skin. In some embodiments, the flexible substrate 105 may be formed of or include at least one of foam, silicone, soft plastic, rubber or elastomers.

As illustrated in FIG. 8, an adhesive layer or backing 220 may overlay the lower surface 215 of the flexible substrate 205. In some embodiments, the adhesive layer or backing 220 may be adhered, fastened or otherwise attached to the lower surface 215 of the flexible substrate 205. However, the various embodiments of the present disclosure are not limited to the aforementioned configuration. In some embodiments, the adhesive layer or backing 220 may be in the form of a coating, for example, an adhesive coated onto the lower surface 215 of the flexible substrate 205. The adhesive layer or backing 220 may include an adhesive for adhering the holder 200 having an intravenous needle assembly and associated connector (e.g., Luer fitting) to skin of the patient 50.

In some embodiments, a solvent pathway 225 may be integrated into at least a portion of the adhesive layer or backing 220. As depicted, the solvent pathway 225 is integrated throughout the adhesive layer or backing 220. However, the various embodiments of the present disclosure are not limited to the aforementioned configuration. In some embodiments, the solvent pathway 225 may be integrated into only a portion of the adhesive layer or backing 220.

The holder 200 may include at least one solvent delivery line 255 coupled to the upper surface 210 of the flexible substrate 205. As depicted, one solvent delivery line 255 may be coupled to the upper surface 210. The various embodiments of the present disclosure however are not limited to the aforementioned configuration. In some embodiments, the holder 200 may include more than one solvent delivery line 255. The solvent delivery line 255 may be configured to transport a solvent from a solvent source (e.g., a syringe) into the solvent pathway 225. Accordingly, the solvent pathway 225 may include at least one aperture 235 for fluidly connecting the solvent delivery line 255 and the solvent pathway 225. As depicted, the solvent pathway 225 includes one aperture 225. However, the various embodiments of the present disclosure are not limited to the aforementioned configuration. In some embodiments, the solvent pathway 225 may include more than one aperture 235. As depicted, the solvent delivery line 255 may have a hollow interior which is fluidly communicated with the solvent pathway 225 that is integrated into the adhesive layer or backing 120. Accordingly, the solvent delivery line 255 may be a vessel for transporting solvent from the solvent source (e.g., syringe) into the solvent pathway 225 of adhesive layer or backing 220 via the aperture 235. The solvent pathway may be interposed between the patient's skin and the adhesive layer or backing 220 when the holder 200 is adhered to the patient's skin. The solvent may be capable of breaking down or otherwise dissolving the adhesive in the adhesive layer or backing 205 when the solvent is absorbed into the solvent pathway 225, as shall be described in further detail below. In some embodiments, the solvent may be isopropyl alcohol.

According to various embodiments of the present disclosure, the solvent delivery line may have a first end 260 with a syringe connection portion 265 and a second end 250 coupled to the at least one aperture 235. As depicted, the syringe connection portion 265 may be formed as a housing adapted to receive a syringe containing the solvent configured to dissolve and break down at least a portion of the adhesive layer or backing 220.

According to various aspects of the present disclosure, the holder 200 may further include a connector 240 secured to the upper surface 210 of the flexible substrate 205. The connector 240 may have a first end 145 for connection to a needle assembly (e.g., a catheter) and a second end 150 for connection to an IV fluid line (e.g., IV supply line 5). For example, the connector 240 may be a luer lock fitting, and in particular may be, but not limited to, a male luer lock fitting. In these embodiments, the first end 145 of the male luer lock fitting may have a spin lock collar 155 for threaded engagement and connection of a needle assembly (e.g., catheter or other needle device) to be inserted into the body of the patient 50 through the skin. Accordingly, a needle assembly may be attached or adhered to the patient's skin via the holder 200. The aforementioned configuration is advantageous over prior art dressings and adhesive methods (e.g., taping) of needles and needle assemblies which directly adhere the needle assembly and associated connector (e.g., male luer lock fitting) to the patient's skin. For example, by incorporating the securement mechanism in the male luer lock fitting (i.e., by connecting the needle assembly to the holder 200 via the luer lock fitting 240 and then attaching the holder 200 to the patient), further isolation may be provided in cases where the needle assembly that is being used contains a short extension tube. Given the aforementioned configuration of the holder 200, the short extension tube may filter out small dynamic loads and thereby not impart these loads onto the needle assembly that is inserted into the patient.

While not strictly necessary, there may be a benefit to be obtained if the holder 200 is longer (i.e., in the Y direction) than it is wide (i.e., in the X direction). A narrower width may provide for better support and securement of the holder 200. Additionally, a longer length may allow for added versatility in the positioning of the holder 200 relative to the luer lock fitting 240.

In operation, a needle assembly (e.g., a catheter or other needle device to be inserted into the body of a patient) may be threadedly engaged to the first end 145 of the luer lock fitting 240 via the spin lock collar 155. The lower surface 215 of holder 200 may then be pressed against the skin of the patient to expose and adhere the adhesive layer or backing 220 to the patient's skin. Accordingly, the needle assembly may be securely attached or adhered to the patient's skin via the holder 200. The IV supply line 5 may then be connected to the second end 150 of the luer lock fitting 240 in order to deliver a fluid or other drug from the IV supply line 5 to the patient via the needle assembly. Once the fluid has been administered to and/or removed from the patient's body via the needle assembly, the holder 200 may be detached from the patient's skin as detailed below. In the event that it is necessary to detach the needle assembly from the luer lock fitting 240 for service and/or to clear a needle of the needle assembly, the luer lock fitting 240 may be unthreaded from the needle assembly via the spin lock collar 155.

When it is desired to remove the holder 200 from the patient's skin, a syringe containing the solvent may be connected or otherwise attached to the syringe connection portion 265. The solvent may then be injected from the syringe into the solvent delivery line 255 and transported to the solvent pathway 225 via the aperture 250. Accordingly, the solvent may flow from the solvent pathway 225 into the adhesive layer or backing 220. In particular, the solvent may flow into and be absorbed throughout the legs 230 and 240 of the solvent pathway 225. The solvent may then begin to dissolve the adhesive of the adhesive layer or backing 220, which bonds the luer lock fitting 240 to the patient's skin. As the solvent is delivered into the solvent pathway 225, the flexible substrate 205 may balloon or otherwise expand, allowing the solvent to reach further parts of the adhesive layer or backing 220 and gently dissolve & peel away the adhesive layer or backing 220 throughout the holder 200.

Since the solvent dissolves and breaks down the adhesive and causes the lower surface of the flexible substrate 205 to balloon and peel away from the patient's skin, the clinician or other user may advantageously be able to remove the male luer lock fitting 240 from the patient's skin without causing damage or pain. Further advantageously, the aforementioned method of detaching the holder 200 from the patient's skin may allow a stronger adhesive to be used without risk or hurting or damaging the patient's skin as may be the case with conventional securement methods. Furthermore, the adhesive layer or backing 220 provides a securement method which further reduces the risk of needle assembly (e.g., catheter or other needle device) dislodgment.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A holder for securing a venous access device to a patient, the holder comprising:
   a flexible substrate having an upper surface, a lower surface, and an outer perimetal surface between the upper and lower surfaces;
   an adhesive layer overlaying the lower surface of the flexible substrate, the adhesive layer having an adhesive for adhering to skin of the patient;
   a hydrophilic matrix integrated into at least a portion of the adhesive layer;
   at least one solvent reservoir, disposed on the upper surface of the flexible substrate, an aperture between the at least one solvent reservoir and the adhesive layer, and a reservoir base obstructing the aperture, wherein the reservoir base is removable from the at least one solvent reservoir to permit movement of a solvent from the at least one solvent reservoir to the adhesive layer; and
   a connector secured to the outer perimetal surface, the connector comprising a first end for connection to a needle assembly and a second end for connection to an IV fluid line.

2. The holder of claim 1, wherein the flexible substrate comprises at least one of foam, silicone, soft plastic, rubber or elastomers.

3. The holder of claim 1, wherein the at least one solvent reservoir comprises a solvent configured to dissolve and break down at least a portion of the adhesive layer.

4. The holder of claim 3, wherein the hydrophilic matrix comprises a hydrophilic material capable of absorbing the solvent.

5. The holder of claim 3, wherein the solvent comprises isopropyl alcohol.

6. The holder of claim 1, wherein the connector comprises a luer lock connector.

* * * * *